United States Patent [19]

Weigel

[11] Patent Number: 5,505,089
[45] Date of Patent: Apr. 9, 1996

[54] SCANNER HEAD ASSEMBLY AND COUPLANT SYSTEM THEREFORE

[75] Inventor: Larry A. Weigel, Fullerton, Calif.

[73] Assignee: Rohrback Cosasco Systems, Inc., Sante Fe Springs, Calif.

[21] Appl. No.: 317,348

[22] Filed: Oct. 4, 1994

[51] Int. Cl.$^6$ ................................................ G01N 29/04
[52] U.S. Cl. .................................... 73/635; 73/639
[58] Field of Search .......................... 73/635, 639, 644, 73/637, 638, 629, 620, 621, 622

[56] References Cited

U.S. PATENT DOCUMENTS 3,616,684  11/1971  Nusbickel, Jr. ............................ 73/635
3,958,451   5/1976  Richardson ............................... 73/637
4,149,419   4/1979  Connell, Jr. .............................. 73/639
4,625,557  12/1986  Rutherford ............................... 73/635

*Primary Examiner*—Hezron E. Williams
*Assistant Examiner*—Christine K. Oda

[57] ABSTRACT

A scanner head for ultrasonic imaging of structures generates a display through an ultrasonic transceiver. The scanner head includes a transducer adapted to engage the surface of the structure. Rollers are positioned fore and aft the transducer, and one roller drives a position increment signal generator which drives the transceiver and display circuitry. A couplant delivery system includes nozzles bracketing the transducer in the direction of movement of the scanner head. The flow is controlled by a single valve on top of the head. In this manner, couplant in the desired amount is delivered correctly and concurrently as scanning proceeds.

18 Claims, 2 Drawing Sheets

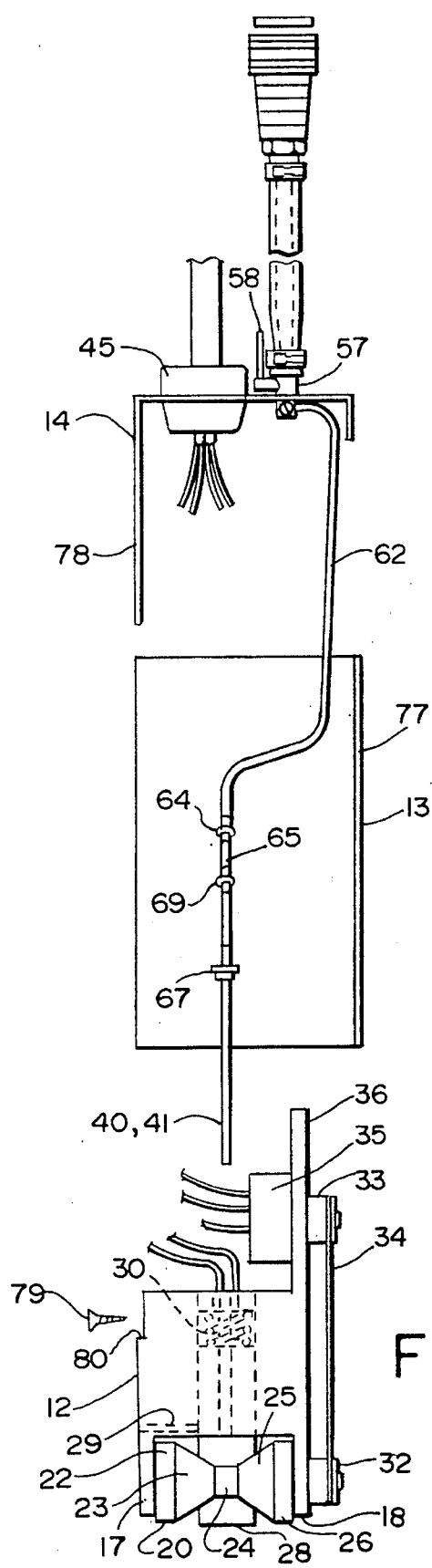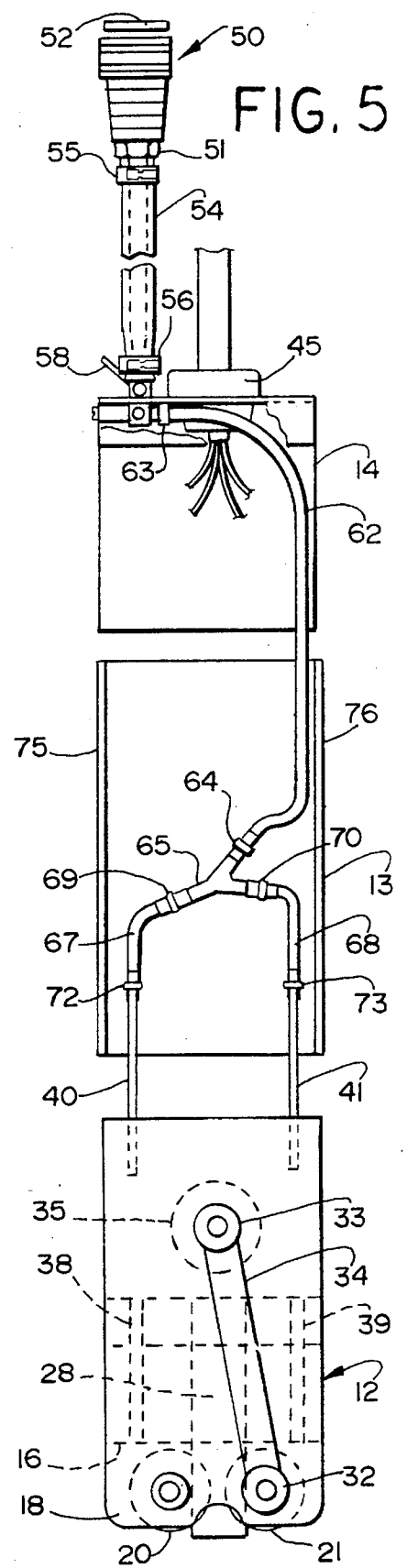
FIG. 4
FIG. 5

SCANNER HEAD ASSEMBLY AND COUPLANT SYSTEM THEREFORE

DISCLOSURE

This invention relates generally as indicated to a scanner head assembly, and more particularly to an ultrasonic scanner head and couplant bubbler system therefor.

BACKGROUND OF THE INVENTION

This invention relates to a scanner head for an ultrasonic imaging system such as shown in Rutherford U.S. Pat. No. 4,625,557. In such prior patent, there is disclosed an acoustical imaging system which is useful, for example, in imaging the thickness and defects in structures such as pipes or pipelines. Such imaging system uses a scanner head which includes a position encoder which provides distance increments signals as the scanner head is moved over the surface. The encoder is driven by a roller on the scanner head which runs against the surface of the pipe or other object being analyzed. The position encoder drives the ultrasonic transceiver and display circuitry. The scanner head may move in opposite directions on rollers, and being hand held, in any direction.

Unfortunately a major shortcoming of ultrasonic transducers is that the surface of the object being analyzed must have ultrasonic couplant applied to limit the acoustic impedance of air. The amount and nature of the couplant may vary widely depending on many factors such as the shape of the surface, type of surface of the structure being analyzed, the temperature of the structure, or ambient temperature. Moreover, excess temperatures may be deleterious to the scanner head. Excess heat can, for example, cause transducer crystals to expand. This can alter measurements taken and give false readings, and reduce the useful life of the system.

In the system of such prior patent, the scanner head is designed to be at least hand held and to move in any direction forward or backward. The operator moving the scanner head is also usually observing the image created. Thus, the manual application of couplant to the structure being analyzed significantly slows the analytical process. Since the scanner head is designed to move along in real-time, the couplant delivery system should accommodate, for example, a 17 inch per second ultrasonic scanning, all without distracting, limiting, or slowing the operator.

SUMMARY OF THE INVENTION

A scanner head for an ultrasonic imaging system includes a linear increment or position encoder which drives the ultrasonic transceiver and display circuitry, but which also includes an ultrasonic couplant delivery system which provides the operator with a convenient accessible single control to adjust couplant flow. The adjustment may be from a few drops to flooding. Two couplant nozzles are positioned slightly spaced and symmetrical of the transducer-structure interface. The nozzles extended generally perpendicular to and outside the axles of the rollers supporting the scanner head. Therefore, there is always a nozzle in front of the transducer regardless of direction. This allows the operator complete freedom of movement since scanning does not have to be limited to preapplied areas of application of the couplant.

Couplant flow rates are adjusted from such few drops or a light mist to flooding to allow for the ultrasonic inspection of structures or materials with temperature ranges of about 30° F. to about 250° F., for example. Couplant flow will be sufficient to ensure transducer crystals are cooled minimizing crystal expansion, thus maintaining accurate linear thickness measurements up to 250° F. The dual jetted couplant flow provides for multiple directional scanner head movement, at over 17 inches per second scanning rate. The couplant system may incorporate the use of water, aqueous solutions, oils, cold weather inhibitors, wetting agents, or other additives.

To the accomplishment of the foregoing and related ends the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

BRIEF DESCRIPTION OF THE DRAWINGS

FIG. 4 is an exploded view of the components of the scanner head illustrating the nozzles before final assembly; and FIG. 5 is a similar exploded view as seen from the right hand side of FIG. 4.

DETAILED DESCRIPTION OF THE PREFERRED EMBODIMENTS

Figures 1, 2:
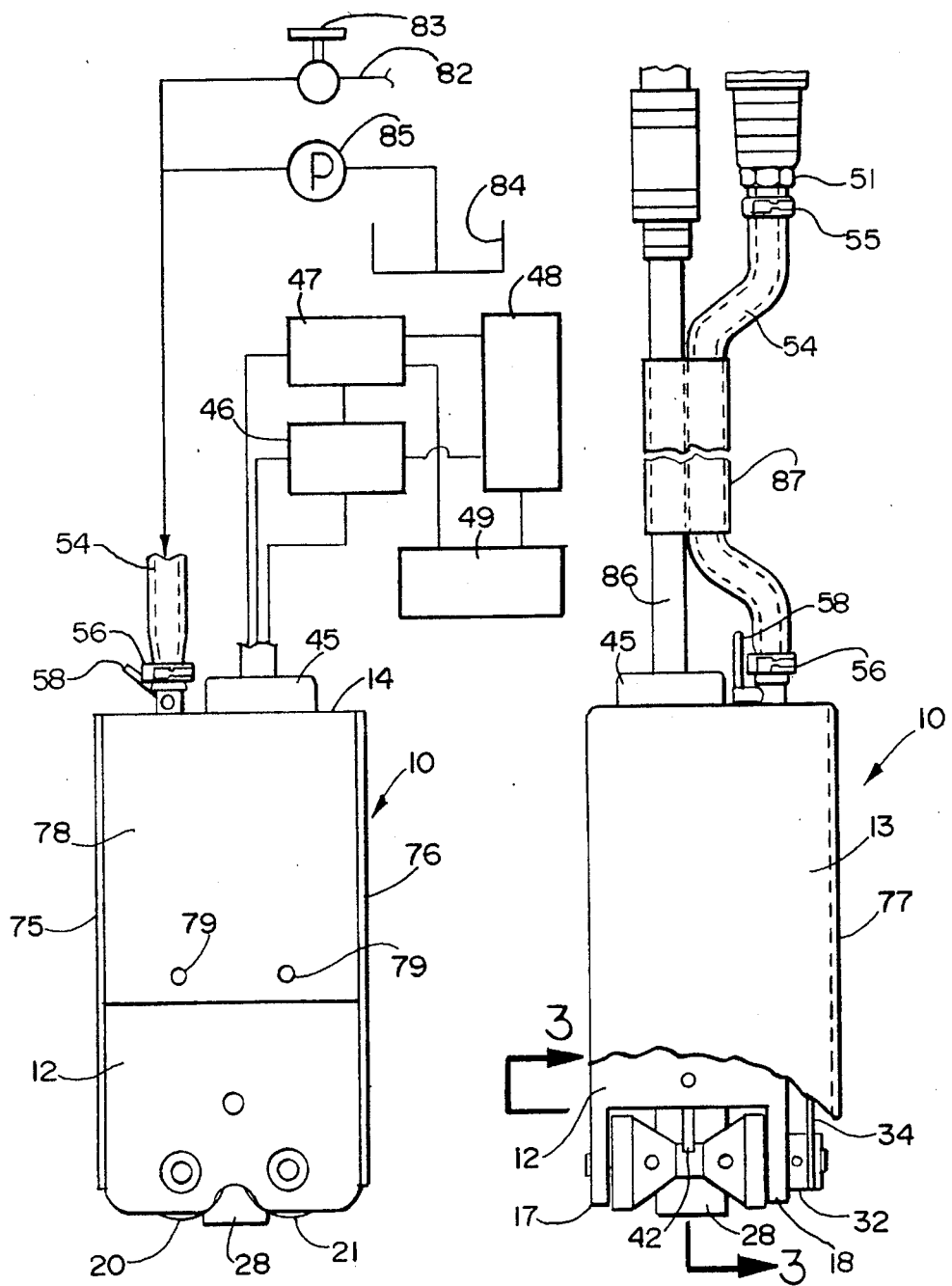
FIG. 1 is a side elevation of a scanner head in accordance with the present invention.
FIG. 2 is an end elevation of the head with the lower part of the shroud partially broken away.
Figure 3:
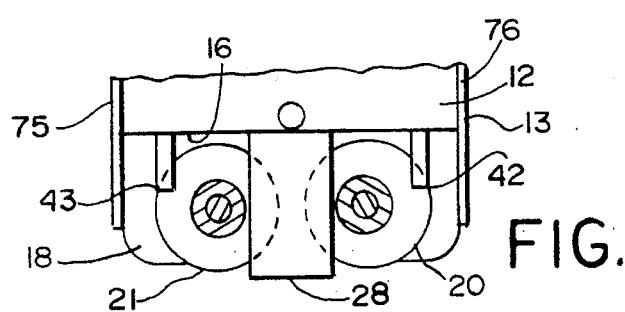
FIG. 3 is a fragmentary enlarged section taken on the line 3—3 of FIG. 2 illustrating the position of the nozzles with respect to the rollers and transducer.

Referring now to the drawings and initially to FIGS. 1–3, there is illustrated generally at 10 an ultrasonic scanner head in accordance with the present invention. The scanner head illustrated is actually relatively small and is designed to be hand held. The actual dimensions of the scanner head are somewhat over 2 inches in width and length and approximately twice that in vertical height.

The elements of the scanner head are a frame 12 housing the principle components, a shroud or cover 13, and a cap or top 14. The assembly of these components is shown more clearly in FIGS. 4 and 5.

Referring now additionally to FIGS. 4 and 5, it will be seen that the frame 12 may comprise a machined block of aluminum alloy, for example, which along its lower end includes a channel 16 forming depending side plates 17 and 18, between which rollers 20 and 21 are journaled. Reading from left to right in FIG. 4 each roller comprises a cylindrical rim section 22, a conical section 23, a center smaller section 24, an opposite conical section 25, and an opposite rim portion 26. Thus each roller has a truncated V configuration with the conical portions forming a set facing each other. Transducer 28 projects downwardly from the frame 12 between such rollers and is nested closely between the opposite conical surface sets. The transducer is mounted in the frame for vertical movement and such vertical movement is limited by set screw or stop screw 29. The transducer is urged downwardly by one or more compression springs seen at 30.

The axle of roller 21 also drives pulley 32 on the exterior of the frame plate 18. The pulley 32 drives another pulley 33 through belt 34 in a one-to-one ratio. The pulley 33 drives optical encoder 35 mounted on the inside of the upwardly extending plate projection 36 of the frame 12.

The frame also includes two vertically extending holes seen at 38 and 39. Such holes are parallel and are aligned with the axis of the transducer, which is in the direction of movement afforded by the rollers 20 and 21. The holes are also such that they are pointing between the opposed conical sections of the rollers to the outside of the transducer. Such holes accommodate couplant nozzles 40 and 41. The tips of the nozzles are indicated in FIG. 3 in the assembled condition at 42 and 43 and they bracket the transducer in the direction of movement afforded by the rollers.

As seen in FIG. 1, the wiring for the transducer 28 and encoder 35 extends through strain relief 45. As shown schematically, the encoder drives a transceiver 46 which creates the pulse for the transducer which is also connected to sampling circuits 47, both being connected to storage means 48, and through such storage means to the display 49. The details of such imaging system are shown in prior Rutherford U.S. Pat. No. 4,625,557. In any event, the encoder 35 of the ultrasonic imaging system is a linear increment or positioning encoder which drives the ultrasonic transceiver and display circuitry.

The couplant system which is seen more clearly in FIGS. 4 and 5 includes a female hose coupling indicated at 50 into which a reducer 51 has been brazed. A rubber gasket indicated at 52 may be used in connection with the coupling 50.

A section of tubing indicated at 54 is clamped at its upper end by hose clamp 55 to the reducer 51, and at its lower end by hose clamp 56 to valve 57. The valve 57 it is a small ball valve, for example, and is opened and closed by movement of the handle 58. The valve 57 is secured to the cap 14. Typically, the handle 58 moves through a 90° arc and the valve is fully open in one extreme and fully closed in the other extreme. At any intermediate setting, the flow is determined by the handle position so that flow through the valve may be as slight as a few drops or a mist, or a full flood.

Within the cap 14 a section of tubing indicated at 62 is secured to the valve by clamp 63. The opposite end of the tube section is secured by clamp 64 to one leg of a flow splitter which is a Y-fitting 65.

Short sections of tubing indicated at 67 and 68 are connected to the stem and opposite leg of the Y-fitting by clamps 69 and 70, respectively. The lower ends of the tubing section 67 and 68 are connected by clamps 72 and 73 to nozzle tubing 40 and 41, respectively. A Y-fitting, as illustrated, is selected to give the proper spacing or span to the parallel nozzles tubes 40 and 41 and still clear the wiring coming from the encoder and transducer.

In assembly, the nozzle tubes 40 and 41, which may for example be ⅛ inch brass tubes, are inserted in the holes 38 and 39, and held in place by a suitable epoxy cement. In this manner, the clamps 72 and 73 being carefully positioned at the tops of the nozzle tubes, act as stops to position the opposite ends at the locations 42 and 43 seen in FIG. 3.

The shroud or cover 13 is simply U-shape with the legs seen at 75 and 76 while the back or bight portion is seen at 77. The shroud or cover is held to the frame when assembled by suitable fasteners not shown. The cap 14 is positioned in place with the longer downwardly extending side 78 is held in place by fasteners 79 when such side fits within the shoulder shown at 80 in FIG. 4. When the shroud and cap are in place, it will be seen that the shroud provides a skirt around which has sufficient clearance at its bight portion to enclose yet clear the pulleys 32 and 33 as well as the belt 34.

Referring back to FIG. 1, it will be seen that the couplant may be provided from a water line indicated at 82 through valve 83 or the couplant may be secured from a tank 84 through a pump 85. The use of a tank allows additives to be mixed with the couplant such as aqueous solutions, oils, cold weather inhibitors, or wetting agents. As seen in FIG. 2, the coupling tubing 54 and the wiring harness 86 above the scanner head may be secured together by a shrink wrap 87 for convenience.

It can now be seen that the present invention incorporates a couplant delivery system into the scanner head which allows the scanner operator to adjust the couplant flow from a few drops or a mist to a flooding of an area. The couplant nozzles are installed in the scanner head at strategic positions fore and aft the direction of movement of the transducer which allows complete freedom of movement and application since couplant is supplied as the scanning takes place.

The couplant flow rates may be adjusted through a complete range and permit ultrasonic inspection of structures with temperature ranges of from about 30° F. to about 250° F. Moreover, the couplant flow is such that it will ensure transducer crystals are cooled minimizing crystal expansion, thus maintaining the accuracy of linear thickness measurements up to about 250° F. The couplant system is such that it can readily keep up with the system moving along a surface in real time and may accommodate a 17-inch per second ultrasonic scanning. The couplant system also readily permits the use of water, oils, cold weather inhibitors, wetting agents, or other additives.

Although the invention has been shown and described with respect to certain preferred embodiments, it is obvious that equivalent alterations and modifications will occur to others skilled in the art upon the reading and understanding of this specification. The present invention includes all such equivalent alterations and modifications, and is limited only by the scope of the claims.

What is claimed is:

1. A scanner head for ultrasonic analysis of structures comprising a frame, a transducer projecting from the frame, and roller means for supporting the head to be reciprocated over the surface of the structure to be analyzed with the transducer in contact with the structure, said roller means driving an encoder to create distance increment signals, and two couplant delivery nozzles to supply couplant to the surface being analyzed, one nozzle being fore and one nozzle being aft of the transducer in the direction of such reciprocation.

2. A scanner head as set forth in claim 1 wherein said roller means for supporting the head includes two rollers, one fore and one aft of the transducer.

3. A scanner head as set forth in claim 2 wherein said two couplant delivery nozzles point at the surface being analyzed aligned with the direction of reciprocation fore and aft the transducer.

4. A scanner head as set forth in claim 3 wherein each nozzle is just outboard of one of said rollers.

5. A scanner head as set forth in claim 4 including control means on top of said scanner head to control the flow of said couplant.

6. A scanner head as set forth in claim 5 wherein said control means comprises a single valve to control the flow of said couplant through both said nozzles concurrently.

7. A scanner head for ultrasonic analysis of structures by generating a display through an ultrasonic transceiver comprising a portable frame, a transducer projecting from the frame and engaging the surface of the structure, roller sets mounted on said frame fore and aft of said transducer supporting said head for movement over the surface of the structure, one of said roller sets driving a position increment signal generator which drives the ultrasonic transceiver and display circuitry, and a couplant delivery system for said scanning head comprising couplant delivery nozzles fore and aft of said transducer, said nozzles being aligned in the direction of movement afforded by said roller sets.

8. A scanner head as set forth in claim 7 wherein said roller sets are in part conical forming conical portions, with the conical portions of each roller set facing each other, whereby the curvature of a surface being analyzed may project between said conical portions of each roller set.

9. A scanner head as set forth in claim 8 wherein said transducer projects closely adjacent said conical portions of said roller sets, and each said nozzle also projects between said conical portions of a respective roller set.

10. A scanner head as set forth in claim 9 including a couplant valve on said head operative to control the flow of couplant through each said nozzles.

11. A scanner head for ultrasonic analysis of structures comprising a frame supporting a transducer for engagement with the structure, a roller having an axis of rotation mounted on said frame also for engagement with said structure, said roller supporting said frame for movement over said structure and driving a position encoder signal generator, as said scanner head is traversed across the structure, and a couplant dispenser at two points fore and aft of the transducer, said two points being aligned substantially normal to the axis of rotation of said roller.

12. A scanner head as set forth in claim 11 wherein said dispenser includes nozzles at said two points, and single valve means on said head to control the flow of couplant through both said nozzles.

13. A scanner head as set forth in claim 12 including a single outlet from said single valve, and a flow splitter connecting said outlet and each said nozzle.

14. A scanner head as set forth in claim 13 wherein said nozzles are the ends of parallel lengths of tubing, said flow splitter substantially spanning the distance between said tubing.

15. A method of analyzing a structure for defects and thickness comprising the steps of creating an ultrasonic image through a transceiver and display circuitry representative of said defects and thickness by traversing a scanner head across the surface of the structure with the scanner head including a transducer in engagement with the surface, and using a distance increment signal generator to pulse the transducer and drive the transceiver and display circuitry, and supplying couplant through the scanner head through two nozzles to the structure surface in line with the direction of traverse across the surface of the structure directly and immediately ahead of the transducer regardless of the direction concurrently as the scanner head is traversed.

16. A method as set forth in claim 15 including the step of supplying couplant to the surface immediately ahead of and behind the transducer regardless of the direction.

17. A method as set forth in claim 15 including the step of controlling the flow of couplant from the scanner head.

18. A method as set forth in claim 15 including the step of controlling the flow of couplant from a valve on top of the scanner head.

\* \* \* \* \*